United States Patent
Parthasaradhi et al.

(10) Patent No.: US 7,053,115 B2
(45) Date of Patent: May 30, 2006

(54) CRYSTALLINE FORM OF DORZOLAMIDE HYDROCHLORIDE

(75) Inventors: Reddy Bandi Parthasaradhi, Hyderabad (IN); Reddy Kura Rathnakar, Hyderabad (IN); Reddy Rapolu Raji, Hyderabad (IN); Reddy Dasari Muralidhara, Hyderabad (IN); Reddy Itiyata Srinivas, Hyderabad (IN)

(73) Assignee: Hetero Drugs Limited, Andhrapradesh (IN)

( * ) Notice: Subject to any disclaimer, the term of this patent is extended or adjusted under 35 U.S.C. 154(b) by 135 days.

(21) Appl. No.: 10/250,591

(22) PCT Filed: Apr. 7, 2003

(86) PCT No.: PCT/IN03/00144

§ 371 (c)(1),
(2), (4) Date: Jul. 2, 2003

(87) PCT Pub. No.: WO2004/089957

PCT Pub. Date: Oct. 21, 2004

(65) Prior Publication Data

US 2004/0198805 A1    Oct. 7, 2004

(51) Int. Cl.
*C07D 495/04* (2006.01)
(52) U.S. Cl. ............................ 514/432; 549/23; 549/28
(58) Field of Classification Search ................ 514/432; 549/23, 28
See application file for complete search history.

(56) References Cited

U.S. PATENT DOCUMENTS

| | | |
|---|---|---|
| 4,879,288 A | 11/1989 | Warawa et al. |
| 6,372,734 B1 | 4/2002 | Snape et al. |
| 2002/0147186 A1 | 10/2002 | Snape |
| 2003/0216376 A1 | 11/2003 | Lifshitz-Liron et al. |
| 2004/0220400 A1 | 11/2004 | Diller et al. |

FOREIGN PATENT DOCUMENTS

| | | |
|---|---|---|
| EP | 0240 226 | 11/1990 |
| EP | 0282236 | 11/1991 |
| EP | 037 A1 | 9/1994 |
| WO | WO 99/06381 | 2/1999 |
| WO | WO 02/55125 | 8/2001 |
| WO | WO 2004/078735 A1 | 9/2004 |

OTHER PUBLICATIONS

Scozzafava et al. Journal of Medicinal Chemistry. vol. 42, No. 14 (1999), pp. 2641-2650.*
PCT IN 03/00144—International Search Report for PCT Parent Application.
M.P. Quint et al., "Dorsolamide Hydrochloride", Analytical Profiles of Drug Substances and Excipients, 26, 1999, pp. 283-316.
PCT International Search Report Dated Mar. 3, 2003.

* cited by examiner

*Primary Examiner*—Kamal A. Saeed
(74) *Attorney, Agent, or Firm*—Caesar, Rivise, Bernstein, Cohen & Pokotilow, Ltd.

(57) ABSTRACT

The present invention relates to a novel crystalline form of dorzolamide hydrochloride, to processes for its preparation and a pharmaceutical composition containing it.

9 Claims, 1 Drawing Sheet

CRYSTALLINE FORM OF DORZOLAMIDE HYDROCHLORIDE

FIELD OF THE INVENTION

The present invention relates to a novel crystalline form of dorzolamide hydrochloride, to processes for its preparation and a pharmaceutical composition containing it.

BACKGROUND OF THE INVENTION

Dorzolamide hydrochloride, chemically (4S,6S)-4-(ethylamino)-5,6-dihydro-6-methyl-4H-thieno[2,3-b]thiopyran-2-sulfonamide 7,7-dioxide hydrochloride, which has the formula (1):

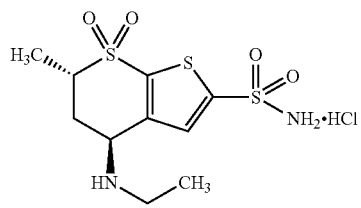

is a carbonic anhydrase inhibitor. Dorzolamide hydrochloride ophthalamic solution is indicated in the treatment of elevated intraocular pressure in patients with ocular hypertension.

Analytical profiles of drug substnaces and excipients, volume 26, p-283–317 mentioned two crystalline forms of dorzolamide hydrochloride (form I, II).

It has now been found that dorzolamide hydrochloride can be prepared in a novel crystalline form (form III). The novel crystalline form is stable and is not spontaneously converted to the previously known forms. The novel form is found to be suitable for pharmaceutical preparations.

The object of the present invention is to provide a stable novel crystalline form of dorzolamide hydrochloride, a process for preparing it and a pharmaceutical composition containing it.

DETAILED DESCRIPTION OF THE INVENTION

According to one aspect of the present invention, there is provided a novel crystalline form of dorzolamide hydrochloride, designated as form III, characterized by an x-ray powder diffraction spectrum having peaks expressed as 2θ at about 5.7, 8.6, 15.5, 16.1, 16.8, 16.9, 17.2, 18.4, 19.0, 21.1, 22.5, 23.2, 25.1, 25.6, 27.3, 28.9 and 30.5 degrees. FIG. 1 shows typical form III x-ray powder diffraction spectrum.

According to another aspect of the present invention, there is provided a process for preparation of the form III of dorzolamide hydrochloride. Thus, dorzolamide hydrochloride form III is precipitated from a solution comprising dorzolamide hydrochloride and dimethylsulfoxide by adding an alcohol to the solution.

The volume of the alcohol required to precipitate dorzolamide hydrochloride depends on the alcohol used, the volume of dimethylsulfoxide relative to the quantity of dorzolamide and the temperature at which precipitation occurs. Thus, at least about 5 ml of isopropyl alcohol is required to precipitate dorzolamide hydrochloride at 25° C. from the solution containing 5.5 gm of dorzolamide hydrochloride and 15 ml of dimethylsulfoxide.

According to another aspect of the present invention there is provided an another process for preparation of dorzolamide hydrochloride form III. Thus, dorzolamide free base is dissolved in dimethylsulfoxide, hydrochloric acid is added to the solution, the contents are maintained for 1 to 5 hours at 0° C. to 20° C., an alcohol is added to the contents and the separated solid is collected by filtration or centrifugation.

The quantity of hydrochloric acid is not critical, but at least 1 mole of hydrochloric acid per mole of dorzolamide is preferable.

The suitable alcohols are methanol, ethanol, isopropyl alcohol, tert-butyl alcohol and n-butyl alcohol. A mixture of alcohols or an alcohol/s mixed with any other solvent may also be used. The preferable solvents are ethanol and isopropyl alcohol.

According to another aspect of the present invention there is provided a pharmaceutical composition comprising dorzolamide hydrochloride form III and a pharmaceutically acceptable carrier.

Figure 1:
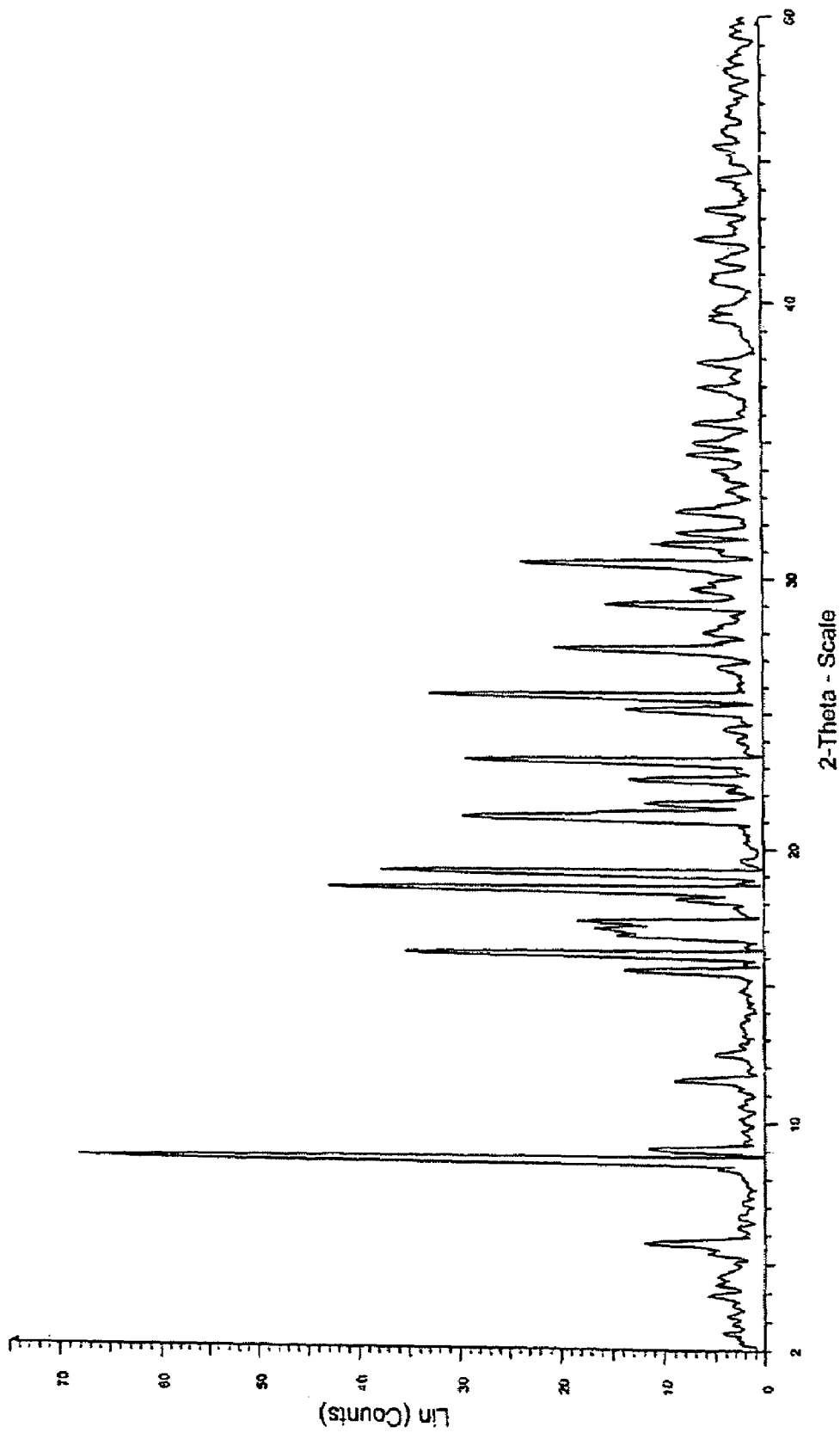
FIG. 1 is a x-ray powder diffraction spectrum of dorzolamide hydrochloride form III.

x-Ray powder diffraction spectrum was measured on a Siemens D5000 x-ray powder diffractometer having a copper-Kα radiation.

The following examples are given for the purpose of illustrating the present invention and should not be considered as limitations on the scope or spirit of the invention.

EXAMPLE 1

Dorzolamide free base (5.0 gm, obtained by the process described in example 24 of U.S. Pat. No. 4,797,413) is dissolved in dimethyl sulfoxide (12 ml) and the pH of the solution is adjusted to 1.0 with conc. hydrochloric acid. The reaction mixture is maintained for 3 hours at 5° C. to 10° C. and then isopropyl alcohol (20 ml) is added. The contents are stirred for 1 hour at 15° C. to 20° C. and the solid is collected by filtration to give 4.0 gm dorzolamide hydrochloride form III.

EXAMPLE 2

Dorzolamide hydrochloride (10 gm, obtained by the process described in example 24 of U.S. Pat. No. 4,797,413) is mixed with dimethylsulfoxide (50 ml) and the contents are heated to 60° C. To the solution so obtained, isopropyl alcohol (60 ml) is added at 25° C. The precipitated crystals are filtered to give 9.1 gm dorzolamide hydrochloride form III.

EXAMPLE 3

Example 2 is repeated substituting dorzolamide hydrochloride form I for dorzolamide hydrochloride to give dorzolamide hydrochloride form III.

EXAMPLE 4

Example 2 is repeated substituting dorzolamide hydrochloride form II for dorzolamide hydrochloride to give dorzolamide hydrochloride form III.

EXAMPLE 5

Dorzolamide free base (5.0 gm, obtained by the process described in example 24 of U.S. Pat. No. 4,797,413) is dissolved in dimethyl sulfoxide (12 ml) and the pH of the solution is adjusted to 1.0 with conc. hydrochloric acid. The reaction mixture is maintained for 3 hours at 5° C. to 10° C. and then ethanol (30 ml) is added. The contents are stirred for 2 hour at 15° C. to 20° C. and the solid is collected by filtration to give 4.0 gm dorzolamide hydrochloride form III.

We claim:

1. A crystalline dorzolamide hydrochloride form III, characterized by an x-ray powder diffraction pattern having peaks expressed as 2θ at 5.7, 8.6, 15.5, 16.1, 16.8, 16.9, 17.2, 18.4, 19.0, 21.1, 22.5, 23.2, 25.1, 25.6, 27.3, 28.9 and 30.5 degrees.

2. A process for preparing the crystalline dorzolamide hydrochloride form III of claim 1, which comprises the step of precipitating dorzolamide hydrochloride form III from a solution comprising dorzolamide hydrochloride and dimethylsulfoxide by adding an alcohol to the solution; wherein the alcohol is selected from the group consisting of methanol, ethanol, isopropyl alcohol, tert-butyl alcohol and n-butyl alcohol.

3. A process according to claim 2, wherein the dorzolamide hydrochloride crystalline form is used to prepare the solution.

4. A process according to claim 2, wherein the alcohol is isopropyl alcohol.

5. A process according to claim 2, wherein the alcohol is ethanol.

6. A process for preparing dorzolamide hydrochloride form III, which comprises the steps of;
  a) dissolving dorzolamide free base in dimethylsulfoxide;
  b) adding hydrochloric acid;
  c) maintaining for 1 to 5 hours at 0° C. to 20° C.;
  d) added adding an alcohol; and
  e) collecting a solid from the contents by filtration or centrifugation;
  wherein the alcohol is selected from the group consisting of methanol, ethanol, isopropyl alcohol, tert-butyl alcohol and n-butyl alcohol.

7. A process according to claim 6, wherein the alcohol is isopropyl alcohol.

8. A process according to claim 6, wherein the alcohol is ethanol.

9. A process according to claim 6, wherein the solid is collected at 15° C. to 20° C.

* * * * *

UNITED STATES PATENT AND TRADEMARK OFFICE
CERTIFICATE OF CORRECTION

PATENT NO. : 7,053,115 B2  
APPLICATION NO. : 10/250591  
DATED : May 30, 2006  
INVENTOR(S) : Bandi Parthasaradhi Reddy et al.

It is certified that error appears in the above-identified patent and that said Letters Patent is hereby corrected as shown below:

Title Page, Item (12)  
Delete "Parthasaradhi et al.", and replace with --Parthasaradhi Reddy et al.--

Title Page, Item (75) Inventors, Should Read:   --Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Itiyala Srinivas Reddy, Hyderabad (IN)--

Signed and Sealed this

Tenth Day of June, 2008

JON W. DUDAS  
*Director of the United States Patent and Trademark Office*